United States Patent [19]

Calton et al.

[11] Patent Number: 5,357,004
[45] Date of Patent: Oct. 18, 1994

[54] COPOLYMERS OF POLYASPARTIC ACID

[75] Inventors: Gary J. Calton, Elkridge; Louis L. Wood, Rockville, both of Md.

[73] Assignee: Srchem Incorporated, Elkridge, Md.

[21] Appl. No.: 195,036

[22] Filed: Feb. 14, 1994

Related U.S. Application Data

[63] Continuation-in-part of Ser. No. 44,900, Apr. 7, 1993, Pat. No. 5,286,810, and a continuation-in-part of Ser. No. 926,242, Aug. 7, 1992, abandoned.

[51] Int. Cl.$^5$ .............................................. C08G 69/48
[52] U.S. Cl. ..................................... 525/435; 525/421; 525/422; 528/310; 528/332; 528/335; 528/345; 528/363
[58] Field of Search ....................... 525/421, 422, 435; 528/310, 332, 335, 345, 363

[56] References Cited

U.S. PATENT DOCUMENTS

| | | | |
|---|---|---|---|
| 3,351,520 | 11/1967 | Spicer et al. | 525/421 |
| 4,585,855 | 4/1986 | Gaku et al. | 528/322 |
| 4,913,828 | 4/1990 | Caswell et al. | 252/88 |
| 5,219,952 | 6/1993 | Koskan et al. | 525/419 |

Primary Examiner—John Kight, II
Assistant Examiner—Shelley A. Dudson
Attorney, Agent, or Firm—William S. Ramsey

[57] ABSTRACT

Higher molecular weight copolymers of polyaspartic acid which are suitable for the inhibition of scale deposition may be obtained by reacting maleic acid and ammonia in a stoichiometric excess, with a diamine or a triamine, at 120°–350° C., preferably 180°–300° C., and then converting the copolymer of polysuccinimide formed to a salt of a copolymer of polyaspartic acid by hydrolysis with a hydroxide. Alkyl or substituted alkyl groups may be incorporated in the backbone of the polymer by adding a alkyl or substituted alkyl monoamine to maleic acid and ammonia and heating at 120° C. or more until polymerization has occurred.

11 Claims, No Drawings

COPOLYMERS OF POLYASPARTIC ACID

CROSS-REFERENCES TO RELATED APPLICATIONS

This is a continuation-in-part of application Ser. No. 08/044,900, filed Apr. 7, 1993, now U.S. Pat. No. 5,286,810 and Ser. No. 07/926,242, filed Aug. 7, 1992, abandoned.

FIELD OF THE INVENTION

This invention relates to a process for the production of copolymers of polysuccinimide, their conversion to salts of copolymers of polyaspartic acid and the use of these materials.

BACKGROUND OF THE INVENTION

The salts of polyaspartic acid have been used for fertilizers and scale inhibition agents. They are particularly useful for the prevention of scale deposition in boiler water, reverse osmosis membranes, detergents and as inhibitors of dental tartar and plaque formation (tartar barrier agents). These materials are readily biodegradable. Economic methods of production of polyaspartic acid having a higher molecular weight is desirable to provide materials having a greater retention on the object wherein inhibition of scale deposition is desired, and to provide greater stability to biodegradation in addition to their intrinsic value for the prevention of scale deposition in boiler water, reverse osmosis membranes, detergents and as inhibitors of dental tartar and plaque formation (tartar barrier agents).

Highly functionalized, yet readily biodegradable materials, which function as inhibitors of scale deposition are desirable for use as fertilizers, in detergents, in water treatment, and in control of tartar.

The problem of obtaining higher molecular weight polymers of amino acids has been given a great deal of thought due to the rapid degradation of these polymers, especially in the mouth. A major drawback to the use of such polymers as antitartar agents is the lifetime that such polymers have in the mouth. Achieving a means by which a higher molecular weight agent can be obtained is desirable from both an economic and a use standpoint.

The usefulness of alkyl derivatives of polyaspartic acid is known, however, economical methods of production are needed.

DESCRIPTION OF RELATED ART

A number of methods of preparation of polyaspartic acid are disclosed in the literature and other patents, however, no mention is made of methods of preparation of copolymers of polyaspartic acid.

U.S. Pat. No. 4,839,461 discloses a method for making polyaspartic acid from maleic acid and ammonia by reacting these constituents In a 1:1–1.5 molar ratio by raising the temperature to 120°–150° C. over a period of 4–6 hours and maintaining it for 0–2 hours. It is further disclosed that temperatures above 140° C. result in elimination of $CO_2$, thus teaching degradation of the material. The molecular weight range obtained by this method was said to be 1,000–4,000 with a cluster at 1,800–2,000. It is further disclosed that this material is useful in the prevention of tarnishing on glass and porcelain articles. Although not stated, it is known that this action would occur as a result of the inhibition of divalent metal ion salt deposition.

Harada, et al (Thermal polycondensation of free amino acids with polyphosphoric acid. Origins Prebiol. systems Their Mol Matrices, Proc. Conf., Wakulla Springs, Fla. 289, 1963) obtained polysuccinimide from aspartic acid and phosphoric acid at temperatures over 100° C. over a time period of 50–250 hrs, but required temperatures over 170° without phosphoric acid being present. Conventional alkaline hydrolysis provided polyaspartic acid. No molecular weight range was given.

Sodium polyaspartate of 6000 molecular weight (MW) was used in the prevention of boiler scale by changing the crystal structure of calcium salts resulting in the formation of a soft scale (Sarig et al, The use of polymers for retardation of scale formation. Natl Counc Res Dev [Rep](Isr.), 150, 1977). Polyaspartic acid was found to be superior to polyglutamate, MW 14,400, polyvinyl sulfonate, MW 5300, and polyacrylic acid, MW 6,000, in that it gave 66% retardation of total scale and 90% retardation of calcium sulfate scale. In addition, the scale formed in the presence of polyaspartate was softer than that produced in the presence of polyacrylate, polyglutamate and polyvinyl sulfonate.

U.S. Pat. No. 5,057,597 discloses a method for the polycondensation of aspartic acid to produce polyaspartic acid by heating the aspartic acid in a fluidized bed reactor to 221° C. for a period of 3–6 hours in a nitrogen atmosphere followed by conventional alkaline hydrolysis.

Kovacs et al. (J. Org. Chem., 25 1084 [1961]) prepared polyaspartic acid by heating aspartic acid to 200° C. in vacuo for a period of 120 hours or in boiling tetralin over a period of 100 hours followed by alkaline hydrolysis. Kovacs et al, showed that the intermediate formed in the thermal polymerization of aspartic acid was polysuccinimide.

U.S. Pat. No. 3,856,380 discloses the preparation of derivatives of polyaspartic acid by reaction with a primary or secondary amine is reacted with polysuccinimide in a solvent such as dimethylformamide, diethylformamide or dimethylacetamide, followed by alkaline hydrolysis.

In a co-pending application Ser. No. 07/882/919, incorporated herein by reference, a method of production of polyaspartic acid is disclosed in which maleic acid and ammonia are heated to 160°–300° C. followed by hydrolysis with a hydroxide.

The prior art does not disclose the synthesis of the high molecular weight copolymers of polyaspartic acid or the high molecular weight copolymers of polysuccinimide of this invention.

U.S. Pat No. 5,175,285 discloses the use of polymers wherein alkyl amines have been reacted with polysuccinimide in a suitable solvent, which form films, for the surface coating of medicinals and foods.

Co-pending U.S. patent application Ser. No. 08/031,856, filed Mar. 16,1993, by Louis L. Wood, incorporated herein by reference, discloses methods of production of copolymers of polyamino acids having a composition of a general formula,

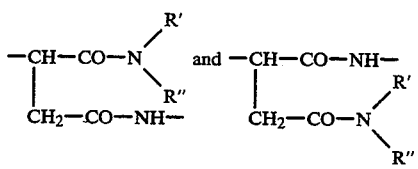

wherein R' is a hydrogen or an alkyl or alkenyl group having 1 to 20 carbons and R" is an alkyl or alkenyl group having 2 to 20 carbons, together with at least one of the groups

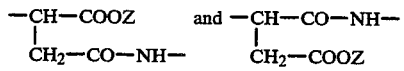

wherein Z represents a hydrogen atom, an alkali metal or an alkaline earth metal or ammonium ion, as a repeating unit have useful properties of inhibition of mineral scale deposition.

U.S. Pat No. 5,266,305 discloses the use of polymers wherein alkyl amines have been reacted with polysuccinimide in a suitable solvent for the Inhibition of tartar formation.

Copending U.S. patent application Ser. No. 07/968,319, filed Oct. 29, 1992, incorporated herein by reference, discloses the use of polymers wherein alkyl amines have been reacted with polysuccinimide in a suitable solvent for the Inhibition of scale formation.

Copending U.S. patent application Ser. No. 08/132,288, filed Oct. 6, 1993, incorporated herein by reference, discloses the use of polymers wherein amino acids have been reacted with maleic acid and ammonia at temperatures above 180° C. for less than four hours.

SUMMARY OF THE INVENTION

High molecular weight copolymers of polysuccinimide were prepared by reacting maleic acid, ammonia and a polyamine at temperatures greater than 120° C. High molecular weight copolymers of polyaspartic acid were prepared by hydrolyzing the polysuccinimide polymers with a hydroxide.

One object of this Invention is to provide a means of preparing copolymers of polysuccinimide. A further object of this invention is to provide a means of preparing copolymers of polyaspartic acid. Yet another object of this invention Is to provide novel compositions which are useful for the inhibition of salt deposition, especially bivalent metal salts, whether in water treatment, detergent addition, oral health care or cosmetic formulation. Yet another object of this Invention is to provide novel compositions which may be further reacted to provide cosmetically useful compounds.

Another object of the Invention Is to provide novel polyamino acid derivatives in which an alkyl or substituted alkyl derivative is Incorporated in the backbone of the polymer. Such alkyl derivatives are novel compositions which are useful as surfactants, foaming agents, solubilizing agents, emulsifying agents, fiber treating agents, dispersants, corrosion Inhibitors, Inhibitors of scale deposition, especially of bivalent metal salts such as $CaSO_4$, $CaCO_3$, $BaSO_4$, $CaPO_4$, and associated mineral scales in water treatment, detergent addition or oral health care, as coatings for pharmaceuticals and foods, as entrapment agents for gas, as control agents for crystallization of Inorganic compounds, or in cosmetic formulation. Such compounds, whether consisting primarily or equally of either $\alpha$ or $\beta$ peptide linkages are effective for such uses.

DETAILED DESCRIPTION OF THE EMBODIMENTS

Higher molecular weight copolymers of polyaspartic acid which are suitable for the inhibition of scale deposition may be obtained by reacting maleic acid and ammonia in a stoichiometric excess, with a compounds having 2 or more primary or secondary amine groups per molecule, at 120°-350° C., preferably 180°-300° C., and then converting the copolymer of polysuccinimide formed to a salt of a copolymer of polyaspartic acid by hydrolysis with a hydroxide. The reaction Is carried out first by the addition of water to maleic anhydride, thus forming maleic acid, or to maleic acid itself, followed by addition of the appropriate amount of ammonia in the form of gaseous ammonia or as its aqueous solution. At this point, the polyamine is added. This solution Is then heated to remove water. As water is removed, the mixture becomes a solid and then a melt of the mixture is formed. Water removal continues as the reaction proceeds and the temperature is brought to 120°-300° C. When the theoretical quantity of water formed in the production of the copolymer of polysuccinimide has been removed, which, depending on the temperature, may occur in even less than 5 minutes, the reaction mixture is allowed to cool. Typically, it may take up to 8 hours at 120° C., whereas it may take less than 5 minutes at 300° C. The copolymer of polysuccinimide formed can be used to make other novel and useful products by reactions such as those described in U.S. Pat. No. 4,363,797, wherein useful derivatives for cosmetic use are described or can be hydrolyzed with metal hydroxides or ammonium hydroxide to provide the appropriate salt of polyaspartic acid. The hydroxides useful in converting the copolymers of polysuccinimide formed above to copolymers of polyaspartic acid include the alkali and alkaline earth metal hydroxides and ammonium hydroxide, and other metal hydroxides, examples of which as their cations are $Na^+$, $K^+$, $Mg^+$, $Li^+$, $Ca^{++}$, $Zn^{++}$, $Ba^{++}$, $Co^{++}$, $Fe^{++}$, $Fe^{+++}$, and $N_4^+$ Solutions of the salts of the copolymers of polyaspartic acid formed in this manner have the same scale inhibition performance and molecular weight range as do the polymers formed by the thermal polymerization of aspartic acid itself. Further manipulation to remove the water or the salts can be carried out to provide water free powders of the salts or the free acid.

Any polyamine may be used to produce these copolymers which has at least two or more primary or secondary amines available for reaction. Preferred polyamines have at least two primary amine groups. Also preferred are polyamines having at least one primary amine and the additional amine groups consist of at least one primary or secondary amine. Suitable polyamines include polyoxyalkyleneamines, polyoxyalkylenediamines or polyoxyalkylenetriamines, melamine, alkyldiamines or alkyltriamines, diethyl triamine, ethylene diamine, and hexanediamine.

The copolymers of polyaspartic acid provided by the present invention are advantageous for inhibition of scale deposition, especially where an increased molecular weight is desirable to provide appropriate biodegradability and retention on surfaces for preventing salt deposition whether in water treatment, detergent additive, oral health care or cosmetic formulation.

These compounds may be used as additives to detergents, to cosmetics and hair treating compositions and to tooth paste. Although the exact mechanism of action of these compounds is not known, it is likely that these high molecular weight copolymers interfere with the crystal structure of salt deposits. Such interference either prevents the deposit of the salt or causes the formation of a soft crystal deposit which is easily removed by water action.

Mono-amines may also be used thus providing novel compositions via incorporation of the alkyl or substituted alkyl amines into the backbone of the polyamino acid. Alkyl amines or substituted alkyl amines having a primary or secondary amine are preferred embodiments of the invention. The incorporation of a ammonia and maleic acid or an equivalent starting compound, such as maleimic acid, malic acid and ammonia, fumaric acid and ammonia, or maleimide, and a mono-amine followed by heating to a temperature above 160° C., preferably above 180° C. or more preferably above 200° C., for a time period sufficient to remove all of the water of polymerization will provide the incorporation of the alkyl or substituted alkyl amine into the backbone of the polymer or at the terminal amide. Removing less than all of the water of polymerization results in a lower molecular weight polymer, but does not necessarily change the properties of the polyamino acid. The polysuccinimide molecule may be water soluble, depending on the amount of water removed.

The effective compounds obtained from this reaction are primarily polyamides having in their molecules at least one of the groups

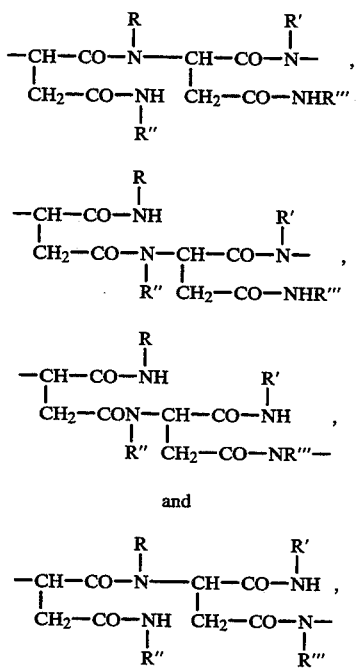

wherein R, R', R" and R'" each is independently a hydrogen or an alkyl or substituted alkyl having 1 to 36 carbons, together with at least one of the groups

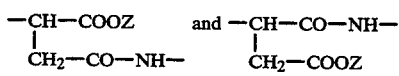

wherein Z represents a hydrogen atom, an alkali metal or an alkaline earth metal or ammonium ion, as a repeating unit.

EXAMPLE 1

Thermal Co-Polymerization of Mono-Ammonium Maleate with Amines

In each case the following procedure was carried out with the indicated amine. A slurry of 19.6 g (0.2 mole) maleic anhydride was dissolved in 40 ml water at 80°–95° C. and stirred for 30 minutes while allowing the mixture to cool to 25° C. To this solution at 25° C. was added 30 g of 30% aqueous solution of ammonium hydroxide (0.22 mol $NH_3$). After thorough mixing, the indicated amine was added in the quantity noted. This solution was evaporated to dryness over a period of 30 minutes. The solid was then heated at 200°–230° C. for 5 minutes, removed from the heat, allowed to cool and broken up with a spatula. The solid was then heated at 235°–245° C. for 10 minutes, removed from the heat, allowed to cool and broken up with a spatula. Finally, the solid was heated at 235°–245° C. for 10–15 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10–20 minutes to give a clear red-brown solution, pH 10–11.0. JEFFAMINE is a trademark of Texaco Chemical Co. for its amines and these amines are defined as follows:

JEFFAMINE T403, Mol. wt. 440, is a triamine made from trimethylolpropane which has been chain extended with propylene oxide and end-capped with primary amines.

JEFFAMINE EDR 148, mol. wt. 148, is a diamine made from triethylene glycol end capped with primary amines.

JEFFAMINE ED 600, mol. wt. 600, is a linear diamine made from a copolymer having approximately 13–14 oxyethylene units and 3–4 oxypropylene units which are endcapped with primary amines.

The copolymer of sodium polyaspartate was tested for inhibition of calcium carbonate precipitation by the calcium drift assay. In this assay a supersaturated solution of calcium carbonate is formed by adding 0.3 ml of a sodium carbonate solution (0.25M $NaHCO_3$ +0.25M $Na_2 CO_3$) to 29.1 ml of 0.55M NaCl and 0.01M KCl containing 0.15 ml of 1.0M $CaCl_2$ and 1.7 ppm of the material to be tested. The reaction is initiated by adjusting the pH to 7.5–8.5 by titration with 1N NaOH and addition of the material to be tested for inhibition of $CaCO_3$ precipitation at a level of 1.7 ppm. At three minutes, the reaction is seeded by the addition of 10 mg of $CaCO_3$ and the pH is recorded. The decrease in pH is directly correlated to the amount of $CaCO_3$ that precipitates. Better Inhibitors show lower changes in pH. The effectiveness of the inhibition is compared to that of sodium polyacrylate, used commercially for the purpose of preventing scale formation.

Table 1 shows the molecular weight measurements, which are given as the time in minutes for the elution of the maximum peak height upon gel permeation chromatography (GPC) of 0.1 to 0.5 mg of each sample dissolved in 8 ml of the aqueous mobile phase. The GPC conditions were: column 1 cm×17.5 cm (15 ml vol), Sephadex G50; aqueous phase of 0.02M $Na_2 HPO_4$/H-

3PO4 adjusted to pH 7.0; flow rate of 0.5 ml/min at 25° C.; detected by UV at 240 nm. The molecular weight standards were aprotinin, 6500 m.w., which eluted at 29 min and poly(sodium L-aspartate), 15,000 m.w. which eluted at 17 minutes.

Table 1 shows the results of these tests with the materials prepared by the method of this Example. The CaCO3 drift values are calculated by subtracting the pH recorded at 20 minutes from the pH recorded at 3 minutes. The yield given is that of polysuccinimide.

TABLE 1

| Sample | Amine Added | Type | Weight of amine (g) | (moles) | Yield (g) | CaCO3 Drift (pH units) | mol. wt. peak (min) |
|---|---|---|---|---|---|---|---|
| none | | | | | | 0.95 | |
| 384-2 | none | | | | 19.5 | 0.29 | 20.5 |
| 5000 mol. wt. polyacrylate | | | | | | 0.10 | |
| 2000 mol. wt. polyacrylate | | | | | | 0.24 | |
| 375-2 | diethylene triamine | diamine | 0.5 | .0048 | 20.3 | 0.21 | 20.6 |
| 375-4 | diethylene triamine | diamine | 1.5 | .0014 | 20.7 | 0.22 | 16 |
| 375-6 | diethylene triamine | diamine | 2.5 | .0024 | 21.2 | 0.21 | 16 |
| 367-2 | JEFFAMINE T-403 | triamine | 1.44 | .003 | 21.4 | 0.31 | 15.5 |
| 367-8 | JEFFAMINE T-403 | triamine | 2.1 | .0048 | 21.3 | 0.27 | 15 |
| 367-6 | JEFFAMINE T-403 | triamine | 2.88 | .006 | 21.2 | gelled | |
| 377-2 | melamine | triamine | 0.6 | .0048 | 20.0 | 0.31 | 24.5 |
| 374-2 | JEFFAMINE EDR 148 | diamine | 1.06 | .007 | 20.3 | 0.20 | 15.5 |
| 374-4 | JEFFAMINE EDR 148 | diamine | 3.18 | .021 | 22.1 | gelled | |
| 381-2 | JEFFAMINE ED600 | diamine | 4.3 | .007 | 23.3 | 0.25 | 16 |
| 382-2 | ethylene diamine | diamine | 0.43 | .007 | 19.7 | 0.27 | 22 |
| 382-4 | ethylene diamine | diamine | 1.29 | .022 | 20.1 | 0.26 | 18 |
| 382-6 | ethylene diamine | diamine | 2.15 | .0358 | 20.9 | 0.36 | 20 |
| 383-2 | ethylene diamine | diamine | 3.0 | .05 | 21.6 | 0.38 | 16.5 |
| 392-2 | hexanediamine | diamine | 1.6 | .014 | 20.9 | 0.42 | 13.9 |

EXAMPLE 2

Thermal Co-Polymerization of Di-Ammonium Maleate with Amines

In each case the following procedure was carried out with the indicated amine. A slurry of 23.2 g (0.2 mole) maleic acid was dissolved in 40 ml water at 8°-95° C. and stirred for 30 minutes while allowing the mixture to cool to 25° C. To this solution at 25° C. was added 60 g of 30% aqueous solution of ammonium hydroxide (0.44 mol NH3). After thorough mixing, the indicated amine was added in the quantity noted. This solution was evaporated to dryness over a period of 30 minutes. The solid was then heated at 200°-230° C. for 5 minutes, removed from the heat, allowed to cool and broken up with a spatula. The solid was then heated at 235°-245° C. for 10 minutes, removed from the heat, allowed to cool and broken up with a spatula. Finally, the solid was heated at 235°-245° C. for 10-15 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10-20 minutes to give a clear red-brown solution, pH 10-11.0 was formed. The results of the resulting polymers were tested for calcium carbonate precipitation and molecular weight as in Example 1.

TABLE 2

| Sample | Amine Added | Type | Weight of amine (g) | (moles) | Yield (g) | CaCO3 Drift (pH units) | mol. wt. peak (min) |
|---|---|---|---|---|---|---|---|
| none | | | | | | 0.95 | |
| 384-2 | none | | | | 19.5 | 0.29 | 20.5 |
| 5000 mol. wt. polyacrylate | | | | | | 0.10 | |
| 2000 mol. wt. polyacrylate | | | | | | 0.24 | |
| 394-2 | diethylene triamine | diamine | 0.5 | .0048 | 19.6 | 0.33 | 21 |

EXAMPLE 3

Reaction of Aspartic acid with Amines

In each case the following procedure was carried out with the indicated amine. A slurry of 26.6 g (0.2 mole) aspartic acid was dissolved in 40 ml water. To this solution at 25° C. was added the indicated amine in the quantity noted. This solution was evaporated to dryness over a period of 30 minutes. The solid was then heated at 235°-245° C. for 30 minutes, removed from the heat, allowed to cool and broken up with a spatula. The solid was then heated at 235°-245° C. for 30 minutes, removed from the heat, allowed to cool and broken up with a spatula. Finally, the solid was heated at 235°-245° C. for 30 minutes, removed from the heat and allowed to cool to room temperature. The resulting water insoluble polymer was slurried in 40.0 ml of water and a solution of 7.6 g of sodium hydroxide in 12 ml of water was added over 5 minutes. The solution was stirred for 10-20 minutes to give a clear reddish-brown solution, pH 10-11.0 was formed. The results of the tests described in Example 1 for these materials are given in Table 3.

TABLE 3

| Sample | Amine Added | Type | Weight of amine (g) | (moles) | Yield (g) | CaCO3 Drift (pH units) | mol. wt. peak (min) |
|---|---|---|---|---|---|---|---|
| none | | | | | | 0.95 | |
| 398-6 | none | | | | 19.5 | 0.21 | 19 |
| | 5000 mol. wt. polyacrylate | | | | | 0.10 | |
| | 2000 mol. wt. polyacrylate | | | | | 0.24 | |
| 394-2 | diethylene triamine | diamine | 0.1 | .001 | 19.5 | 0.21 | 19 |

EXAMPLE 4

Reaction of Maleic Acid, Ammonia and a Mono-Amine

A solution of 0.2 moles of maleic acid was prepared by adding 19.6 g of maleic anhydride to 40 ml of water and allowing to stand for 45 min. To this solution was added 2.58 g (0.02 moles) of n-octyl amine (10 mole % of maleic anhydride) followed by 60 g of 30% ammonium hydroxide. The solution was boiled to dryness over a period of 5 min. The solids were then tumbled at 210°–230° C. for 10 min to give a pink-tan foam. The foam was pulverized and the powder was tumbled at 235°–245° C. for 10 min. The resulting foam was again pulverized and heated for an additional 10 min at 235°–245° C. to give a red tan powder. The powder was placed in 40 g of water and dissolved by the addition of 8.0 g of sodium hydroxide in 12 ml of water to give a dark orange solution. When 0.3 g of this solution was added to 4 g of distilled water and shaken for 30 seconds in a 10 ml test tube, a foam of 2 cm in height was obtained. A control of polyaspartic acid gave no foam.

EXAMPLE 5

Reaction of Maleic Acid, Ammonia and Taurine

A solution of 0.2 moles of maleic acid was prepared by adding 19.6 g of maleic anhydride to 40 ml of water and allowing to stand for 45 min. To this solution was added 2.5 g (0.02 moles) of taurine in 20 ml of water containing 0.8 g of sodium hydroxide (0.02 moles) and 30 g of 30% ammonium hydroxide. The solution was boiled to dryness over a period of 10 min. The solids were then tumbled at 200°–230° C. for 5 min to give a pink-tan foam. The foam was pulverized and the powder was tumbled at 230°–245° C. for 10 min. The resulting foam was again pulverized and heated for an additional 10 min at 235°–245° C. to give 22.7 g of red-tan powder. The powder was placed in 40 g of water and dissolved by the addition of 8.0 g of sodium hydroxide in 12 ml of water to give a dark orange solution.

EXAMPLE 6

Reaction of Maleic Acid, Ammonia and Butyl Amine

A solution of 0.4 moles of maleic acid was prepared by adding 39.2 g of maleic anhydride to 40 ml of water and allowing to stand for 45 min. To this solution was added 6.0 g (0.082 moles) of n-butyl amine. After stirring for 10 min, a solution of 5.4 g (0.382 moles) of ammonia in 35 g of water was added. The solution was heated at 185°–235° C. for 15 min to give a red-brown gum. The solids were pulverized and the powder was tumbled at 205°–235° C. for 15 min to give 40.8 g of red-tan solids. The powder was placed in 65 g of water and dissolved by the addition of 11.8 g of sodium hydroxide in 12 ml of water to give a dark orange solution.

EXAMPLE 7

Reaction of Maleic Acid, Ammonia and Lauryl Amine in Isopropanol

A solution of 39.2 g (0.4 moles) of maleic anhydride in 50 g of isopropanol was stirred for 45 min. To this solution was added 4.6 g (0.025 moles) of dodecylamine. After stirring for 10 min, a solution of 6.4 g (0.375 moles) of ammonia In 40 g of water was added. The solution was heated at 185°–235° C. for two 15 min periods to give 39.1 g of a red-brown solids. The powder was dissolved by placing it in 90 g of water containing 16 g of sodium hydroxide.

EXAMPLE 8

Reaction of Maleic Acid, Ammonia, Diethylene Triamine and Oleyl Amine in Isopropanol A solution of 39.2 g (0.4 moles) of maleic anhydride in 50 g of methanol was stirred for 45 min. To this solution was added 4.0 g of diethylenetriamine and 2.5 g of oleyl amine. After stirring for 10 min, a solution of 6.8 g (0.4 moles) of ammonia in 40 g of water was added. The solution was heated at 190°–235° C. for two 15 min periods to give 42.4 g of a red-brown solids. The powder was dissolved by placing it in 90 g of water containing 16 g of sodium hydroxide. Upon shaking a small amount of the resulting solution in water, a copious foam was observed.

Precipitation Assay for Calcium Sulfate

The material to be tested as an inhibitor of scale formation was added in appropriate quantities to a solution of 5 ml of calcium chloride solutions (21.6 g/L of $CaCl_2$ dihydrate and 41.4 g/L of NaCl) and 5 ml of sulfate solution (20.9 g/L of $Na_2SO_4$ and 41.4 g NaCl). The mixture was then placed in an oven at 160° F. for 12 hours. Finally the mixture was filtered through Whatman #2 paper and dried at 160° F. for 8 hours, after which the weight of precipitate was determined.

Foam Height Test 5 ml of a 100 mg/10ml of the solution to be tested was placed in a 13 mm × 100 mm test tube and shaken for 20 seconds after which the foam height was measured after standing for 30 seconds.

Kaolin Dispersion Test

A suspension of kaolin was prepared by adding 0.2 g of kaolin clay to 5 ml of water and the sample to be tested was added at a final concentration of 20 or 40 ppm in a 12 mm × 100 mm test tube. The test tube was shaken and allowed to stand for 12 hr after which the height of the suspended layer and the compacted solids was measured.

TABLE 4

| Amine Added | Foam Height | Kaolin Dispersion (mm height) compacted | Kaolin Dispersion (mm height) suspended | CaSO4 @2.5 ppm (mg) |
|---|---|---|---|---|
| none | 0 | 17 | 0 | 81 |
| n-butyl | 0 | 3 | 47 | 28 |
| n-octyl | 6 | 4 | 47 | 12 |
| lauryl | 17 | 4 | 48 | 51 |
| oleyl | 9 | 6 | 47 | 15 |

The derivatives are clearly effective in the tests run.

It will be apparent to those skilled in the art that the examples and embodiments described herein are by way of illustration and not of limitation, ant that other examples may be utilized without departing from the spirit and scope of the present invention, as set forth in the appended claims.

I claim:

1. A composition comprising a polyamide having in its molecules at least one of the groups

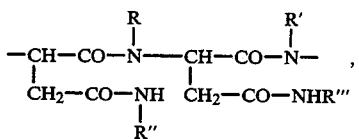

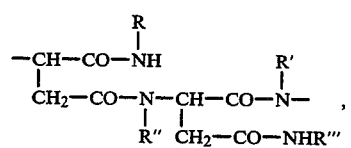

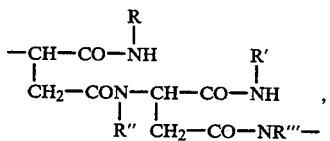

and

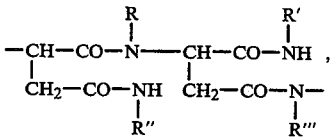

wherein R, R', R" and R'" each is independently a hydrogen or an alkyl or substituted alkyl having 1 to 36 carbons, together with at least one of the groups

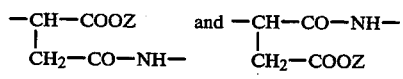

wherein Z represents a hydrogen atom, an alkali metal or an alkaline earth metal or ammonium ion, as a repeating unit, wherein at least one of the R groups is an integral part of an internal peptide bond.

2. A composition comprising a polymer produced by polymerizing (1) maleic acid, (2) ammonia and (3) an alkyl or substituted alkyl amine, at a temperature greater than 120° C. and hydrolyzing the polymer to produce a salt of said polymer.

3. The composition of claim 2 in which said temperature is above 150° C.

4. The composition of claim 2 in which said amine is an alkyl amine.

5. The composition of claim 2 in which said amine is a substituted alkyl amine.

6. A composition comprising a polymer produced by polymerizing (1) maleic acid, (2) ammonia and (3) an alkyl or substituted alkyl amine, at a temperature greater than 120° C.

7. The composition of claim 6 in which said temperature is above 150° C.

8. The composition of claim 6 in which said amine is an alkyl amine.

9. The composition of claim 6 in which said amine is a substituted alkyl amine.

10. A composition comprising a polymer produced by polymerizing (1) maleic acid, (2) ammonia, (3) a polyamine, and (4) an alkyl or substituted alkyl amine, at a temperature greater than 120° C.

11. A composition comprising a polymer produced by polymerizing (1) maleic acid, (2) ammonia, (3) a polyamine and (4) an alkyl or substituted alkyl amine, at a temperature greater than 120° C. and hydrolyzing the polymer to produce a salt of said polymer.

* * * * *